United States Patent
Pelati

(10) Patent No.: US 9,623,392 B2
(45) Date of Patent: Apr. 18, 2017

(54) CATALYST AGGLOMERATION REMEDIATION

(71) Applicant: FINA TECHNOLOGY, INC., Houston, TX (US)

(72) Inventor: Joseph E. Pelati, Houston, TX (US)

(73) Assignee: FINA TECHNOLOGY, INC., Houston, TX (US)

( * ) Notice: Subject to any disclaimer, the term of this patent is extended or adjusted under 35 U.S.C. 154(b) by 210 days.

(21) Appl. No.: 14/642,204

(22) Filed: Mar. 9, 2015

(65) Prior Publication Data

US 2016/0263543 A1    Sep. 15, 2016

(51) Int. Cl.
*B01J 8/04* (2006.01)

(52) U.S. Cl.
CPC .... *B01J 8/0496* (2013.01); *B01J 2208/00371* (2013.01)

(58) Field of Classification Search
None
See application file for complete search history.

(56) References Cited

U.S. PATENT DOCUMENTS

| | | |
|---|---|---|
| 4,347,396 A | 8/1982 | Takano et al. |
| 5,258,348 A | 11/1993 | Van Buren et al. |
| 5,461,179 A | 10/1995 | Chen et al. |
| 2005/0080306 A1 | 4/2005 | Kowaleski et al. |
| 2009/0318741 A1* | 12/2009 | Newman .......... C07B 35/04 585/440 |
| 2009/0318743 A1 | 12/2009 | Arnold et al. |

FOREIGN PATENT DOCUMENTS

WO    0144146 A1    6/2001

OTHER PUBLICATIONS

International Search Report and Written Opinion for Application No. PCT/US2015/019461, dated Jun. 4, 2015, 11 pages.

* cited by examiner

*Primary Examiner* — Tam M Nguyen
(74) *Attorney, Agent, or Firm* — Albert Shung

(57) ABSTRACT

A process may include shutting down a reactor in which ethylbenzene is undergoing dehydrogenation to styrene in the presence of steam and a catalyst adapted to catalyze dehydrogenation of ethylbenzene to styrene. Shutting down the reactor may include reducing a temperature of the reactor. Shutting down the reactor may include supplying a purge stream to the reactor. Supplying a purge stream may include increasing a steam-to-ethylbenzene molar ratio of an input stream to the reactor. Supplying a purge stream may include supplying steam and one or more of $H_2$, $CO_2$, and styrene to the reactor. The process may include stopping supply of the purge stream to the reactor and supplying an inert gas purge stream to the reactor. Shutting down the reactor may be performed without use of a steam-only purge stream.

20 Claims, 2 Drawing Sheets

CATALYST AGGLOMERATION REMEDIATION

FIELD

Embodiments of the present disclosure generally relate to catalyst agglomeration remediation.

BACKGROUND

Polymers of styrene are common and valuable plastics that may be used in the production of items from electronics casing to toys to disposable plates and cups. The chemical formula of styrene monomer is $C_6H_5C_2H_3$, and its structure includes a benzene ring with an attached ethylene group. Styrene is generally produced by dehydrogenation of ethylbenzene. Ethylbenzene has the chemical formula of $C_6H_5C_2H_5$, and its structure includes a benzene ring with an attached ethyl group.

Ethylbenzene dehydrogenation takes place in a dehydrogenation reactor system, which may include one or more dehydrogenation reaction chambers and downstream processing equipment. Superheated steam and ethylbenzene enter the reaction chamber(s) as an input steam where a dehydrogenation catalyst catalyzes the conversion of ethylbenzene to styrene. The mechanism for the dehydrogenation reaction involves the loss of two hydrogen atoms from the ethyl group to form a carbon-carbon double bond. Thus, the chemicals exiting the reaction chamber(s) generally include styrene, hydrogen gas, and steam, as well as unreacted ethylbenzene and other compounds, which may be referred to as styrene offgas.

Occasionally, it may be desirable to subject the dehydrogenation reactor system to a turnaround, also referred to as a shutdown, such as to clean, repair, replace catalyst or otherwise maintain the dehydrogenation reactor system. Generally, a shutdown procedure for a dehydrogenation reactor system includes cooling down the dehydrogenation reaction chambers under a steam-only purge.

Catalyst agglomeration may increase the length of time that it takes to complete a turnaround. Catalyst agglomeration may include the formation clumped catalyst extrudite beds within the dehydrogenation reactor system, which may be fused with potassium. Catalyst agglomeration may be at least in-part caused by potassium migration and long run times of the dehydrogenation reactor system. Without wishing to be bound by theory, potassium is a major catalyst component and may form KOH (potassium hydroxide) with steam at elevated temperatures. KOH has a significant vapor pressure and low melting point, allowing KOH to become mobile at reaction conditions. High potassium content and long run lengths with steam dilution may increase the severity of catalyst agglomeration in dehydrogenation reactor systems.

SUMMARY

An embodiment of the present disclosure includes a process. The process includes shutting down a reactor in which ethylbenzene is undergoing dehydrogenation to styrene in the presence of steam and a catalyst adapted to catalyze dehydrogenation of ethylbenzene to styrene. Shutting down the reactor includes reducing a temperature of the reactor, increasing a steam-to-ethylbenzene molar ratio of an input stream to the reactor to form a purge stream, and supplying the purge stream to the reactor.

An embodiment of the present disclosure includes a process. The process includes shutting down a reactor in which ethylbenzene is undergoing dehydrogenation to styrene in the presence of a catalyst including potassium that is adapted to catalyze dehydrogenation of ethylbenzene to styrene. Shutting down the reactor includes reducing a temperature of the reactor, increasing a steam-to-ethylbenzene molar ratio of an input stream to the reactor to form a purge stream, and supplying the purge stream to the reactor. The process includes stopping supply of the purge stream to the reactor and supplying an inert gas purge stream to the reactor. Shutting down the reactor is performed without use of a steam-only purge stream.

An embodiment of the present disclosure includes a process. The process includes shutting down a reactor in which ethylbenzene is undergoing dehydrogenation to styrene in the presence of a catalyst adapted to catalyze dehydrogenation of ethylbenzene to styrene. Shutting down the reactor includes reducing a temperature of the reactor and supplying a purge stream to the reactor. The purge stream includes steam and one or more of $H_2$, $CO_2$, and styrene.

BRIEF DESCRIPTION OF THE DRAWINGS

The present disclosure may be understood from the following detailed description when read with the accompanying figures.

DETAILED DESCRIPTION

Figure 1:
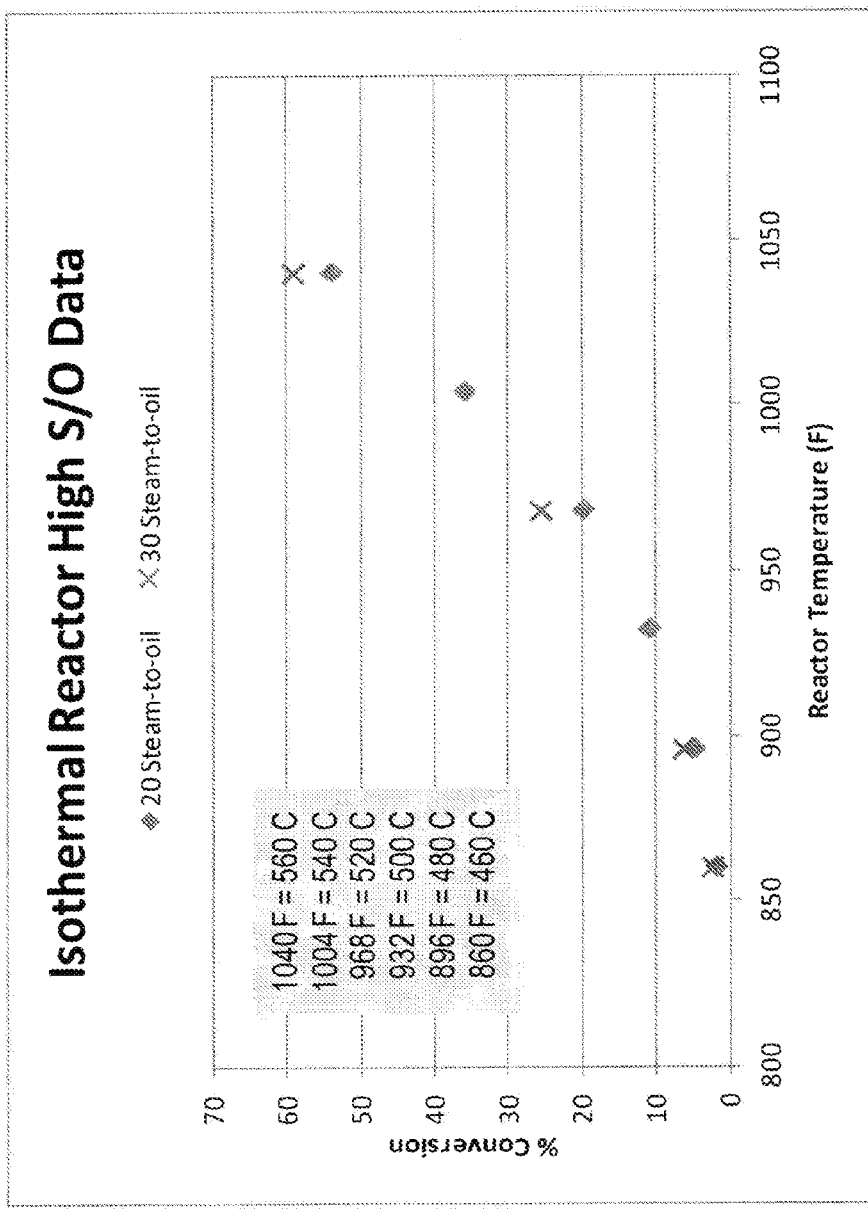
FIG. 1 depicts a plot of percent conversion of ethylbenzene versus reactor temperature for low temperature, high steam-to-oil ratios.

A detailed description will now be provided. The description includes specific embodiments, versions, and examples, but the disclosure is not limited to these embodiments, versions, or examples, which are included to enable a person having ordinary skill in the art to make and use the disclosure when that information is combined with available information and technology.

Various terms as used herein are shown below. To the extent a term used in a claim is not defined below, it should be given the broadest definition skilled persons in the pertinent art have given that term as reflected in printed publications and issued patents at the time of filing. Further, unless otherwise specified, all compounds described herein may be substituted or unsubstituted and the listing of compounds includes derivatives thereof.

Further, various ranges and/or numerical limitations may be expressly stated below. It should be recognized that unless stated otherwise, it is intended that endpoints are to be interchangeable. Further, any ranges include iterative ranges of like magnitude falling within the expressly stated ranges or limitations.

Ethylbenzene dehydrogenation takes place in a dehydrogenation reactor system, which may include one or more dehydrogenation reaction chambers and downstream processing equipment. Superheated steam and ethylbenzene enter the reaction chamber(s) as an input stream where a catalyst catalyzes the conversion of ethylbenzene to styrene. The steam-to-ethylbenzene molar ratio during ethylbenzene dehydrogenation may be at least about 4:1, at least about 5:1, at least about 8:1, or at least about 10:1, for example. The ethylbenzene dehydrogenation reaction is generally run at a temperature of around 500° C. to 650° C. and atmospheric to sub-atmospheric pressure, such as around 5 to 20 psia.

One or more embodiments relate to a process for shutting down a reactor in which ethylbenzene is undergoing dehydrogenation to styrene in the presence of a catalyst adapted to catalyze dehydrogenation of ethylbenzene to styrene.

The process may include reducing a temperature of the reactor. For example and without limitation, the temperature of the reactor may be reduced to a temperature ranging from less than 650° C. to 300° C., or from 575° C. to 360° C., or from 550° C. to 400° C., or from 550° C. to 450° C., or from 500° C. to 450° C., from 500° C. to 460° C. The temperature of the reactor may be reduced to 575° C., 550° C., or 500° C., for example. In certain embodiments, prior to reduction of the temperature of the reactor, the reactor may be operating under reaction conditions.

The process may include using a purge stream in the reactor. Purge stream may include steam and ethylbenzene. For example and without limitation, during dehydrogenation of ethylbenzene to styrene an input stream that includes steam and ethylbenzene may be supplied to the reactor. Supplying purge stream may include adjusting a steam-to-ethylbenzene molar ratio of the input stream to a steam-to-ethylbenzene molar ratio (also referred to as a steam-to-oil molar ratio) of purge stream. For example and without limitation, the steam-to-ethylbenzene molar ratio of purge stream may be greater than the steam-to-ethylbenzene molar ratio of the input stream, and supplying purge steam may include increasing the steam-to-ethylbenzene molar ratio of the input stream. Increasing the steam-to-ethylbenzene molar ratio may include increasing an amount of steam input into the reactor, decreasing an amount of ethylbenzene input into the reactor, or combinations thereof.

In certain embodiments, purge stream may have a steam-to-ethylbenzene molar ratio of from 12:1 to 50:1, or from 15:1 to 40:1, or from 20:1 to 30:1. Purge stream may have a steam-to-ethylbenzene molar ratio of at least 12:1, at least 15:1, at least 20:1, or at least 30:1.

In certain embodiments, the steam-to-ethylbenzene molar ratio of purge stream is maintained at from 12:1 to 50:1 while the temperature of the reactor is further reduced to a temperature ranging from less than 650° C. to 360° C. For example and without limitation, the steam-to-ethylbenzene molar ratio of purge stream may be continuously maintained at from 12:1 to 50:1, or from 15:1 to 40:1, or from 20:1 to 30:1 while the temperature of the reactor is within the range of 550° C. to 450° C. during the shutting down of the reactor.

Purge stream may include steam and one or more of $H_2$, $CO_2$, and styrene. For example and without limitation, one or more of $H_2$, $CO_2$, and styrene may be present as byproducts of dehydrogenation of ethylbenzene, or may be added to steam prior to introduction into the reactor. For example and without limitation, during dehydrogenation of ethylbenzene to styrene the input stream that includes steam and ethylbenzene may be supplied to the reactor. Supplying purge stream may include stopping supply of ethylbenzene to the reactor and adding one or more of $H_2$, $CO_2$, and styrene with the steam. The presence of steam and one or more of $H_2$, $CO_2$, and styrene in purge stream may be maintained while the temperature of the reactor is further reduced to a temperature ranging from less than 650° C. to 360° C. For example and without limitation, the presence of steam and one or more of $H_2$, $CO_2$, and styrene in purge stream may be continuously maintained while the temperature of the reactor is within the range of 550° C. to 450° C. during the shutting down of the reactor.

The supplying of purge stream may begin after the temperature of the reactor is reduced, while the temperature of the reactor is being reduced, or before the temperature of the reactor is reduced.

In certain embodiments, the temperature in the reactor may be held constant while supplying purge stream to the reactor for a period of time ranging from 1 to 24 hours, or from 4 to 18 hours, or from 6 to 16 hours, or from 8 to 14 hours, or from 10 to 12 hours. For example and without limitation, the temperature of the reactor may be held constant prior to a further reduction of the temperature of the reactor.

Shutting down the reactor may be performed without use of a steam-only purge stream. A steam-only purge stream may be a purge stream that includes steam but does not include one or more of ethylbenzene, $H_2$, $CO_2$, and styrene. A steam-only purge stream may be a purge steam that only includes steam. In certain embodiments, shutting down the reactor is performed without use of a steam-only purge stream at conditions where potassium agglomeration is most problematic. Conditions where potassium agglomeration is most problematic may include the presence of steam; temperatures ranging from 400° C. to 600° C., or 425° C. to 575° C., or 450° C. to 550° C., or 475° C. to 525° C., or about 500° C., or combinations thereof. In certain embodiments, shutting down the reactor is performed without use of steam-only purge stream after normal reactor operations have concluded for a short or long term shutdown.

The process may include stopping supply of ethylbenzene to the reactor prior to stopping supply of steam to the reactor. In certain embodiments, the temperature of the reactor may be further reduced after stopping supply of ethylbenzene to the reactor and prior to stopping supply of steam to the reactor.

Shutting down the reactor may include, after supplying purge stream to the reactor, further reducing the temperature of the reactor. For example and without limitation, the temperature of the reactor may be further reduced to a temperature ranging from less than 650° C. to 300° C., or from 575° C. to 360° C., or from 550° C. to 400° C., or from 550° C. to 450° C., or from 500° C. to 450° C., from 500° C. to 460° C. Shutting down the reactor may include continuing to supply purge stream to the reactor while further reducing the temperature of the reactor. Shutting down the reactor may include stopping supply of purge stream to the reactor before further reducing the temperature of the reactor.

The process may include stopping supply of purge stream to the reactor and supplying an inert gas purge stream to the reactor. Inert gas purge stream may include nitrogen, for example. After supplying inert gas purge stream to the reactor, the process may include further reducing the temperature of the reactor. For example and without limitation, the temperature of the reactor may be further reduced to a temperature ranging from 20° C. to 400° C., or to a temperature of at most 400° C., or at most 360° C., or at most 300° C. The temperature in the reactor may be held constant while supplying inert gas purge stream to the reactor for a period of time ranging from 1 to 24 hours, or from 4 to 18 hours, or from 6 to 16 hours, or from 8 to 14 hours, or from 10 to 12 hours. For example and without limitation, the temperature may be held constant prior to a further reduction in the temperature.

In certain embodiments, the steam-to-ethylbenzene molar ratio of purge stream may be continuously maintained at from 12:1 to 50:1 from the time at which purge stream is introduced into the reactor until purge stream is replaced with inert gas purge stream. Inert gas purge stream may be introduced to the reactor subsequent to purge stream having the steam-to-ethylbenzene molar ratio ranging from 12:1 to 50:1, and without any purge streams being introduced to the reactor intermediate of purge stream and inert gas purge stream.

After shutting down the reactor, the catalyst or agglomerated masses of catalyst particles may exhibit an average crush strength that is lower than an average crush strength exhibited by the catalyst prior to shutting down the reactor. For example and without limitation, after shutting down the reactor, the catalyst may exhibit an average crush strength that is at least 10%, or at least 15%, or at least 25%, or at least 40% or at least 50% lower than an average crush strength exhibited by the catalyst prior to shutting down the reactor. Average crush strength may be measured in accordance with ASTM D4179-11.

The catalyst may include one or more of Fe, K, and Ce. For example, the catalyst may include potassium promoted iron oxide. In certain embodiments, the catalyst may primarily include potassium promoted iron oxide. For example and without limitation, the catalyst may include greater than 50, or 60, or 70, or 80, or 90, or 95 weight percent of potassium promoted iron oxide by total weight of the catalyst.

Without wishing to be bound by theory, catalyst agglomeration may be caused by potassium (K) migration. Potassium salts may form KOH at high temperatures in the presence of steam. KOH melts at 360° C. (680° F.) and has considerable vapor pressure which may make KOH mobile under these conditions. Under such conditions, potassium may move out of the catalyst and reactor during the life of the catalyst. When potassium migrates in sufficient quantities to void spaces between catalyst particles, potassium may act as cement that binds the catalyst bed into an agglomerated mass, which may be difficult to remove during turnarounds. Many catalysts used in dehydrogenation of ethylbenzene have long lifetimes, with catalyst runs that may last from 36 to 42 months or longer. Catalyst formulations with high potassium concentration and longer times on stream may allow more potassium migration to occur, which may cause catalyst agglomeration. Certain shutdown procedures may make catalyst agglomeration more severe due to the particular temperatures, purge gasses and specific conditions used. Catalyst agglomeration may cause significant extensions to turnaround schedules, because agglomerated catalyst beds may be cemented with potassium making the unloading of such catalyst beds difficult.

The presence of ethylbenzene in purge steam may cause styrene, $H_2$, $CO_2$, or combinations thereof to form in the reactor during purging of the reactor. Without wishing to be bound by theory, $CO_2$ may convert volatile KOH, a mobile form of potassium, present in the reactor to potassium carbonate, a nonvolatile, immobile form of potassium. Without wishing to be bound by theory, $H_2$ may cause coke removal, iron oxide reduction, KOH inhibition, or combinations thereof, which may reduce catalyst agglomeration.

EXAMPLES

Example 1

Tube Furnace Experiments

Initial exploratory experiments were conducted with a 30" long, horizontal tube furnace and a 1" internal diameter (ID) metal tube reactor with steam injection. Used catalyst samples were wrapped in wire mesh and held in place axially with a metal rod. Water was fed to the unit at 0.5 mL/min at temperatures ranging from 350° C. to 550° C. The reactor was purged with nitrogen at temperature before unloading to keep the samples dry. The used catalyst samples were heated at various temperatures in steam to identify K migration leading to catalyst agglomeration. Particles of used catalyst, when mixed with potassium carbonate, were observed to be cemented together after treatment to qualitatively demonstrate agglomeration. Significant variation in the repeat experiments was caused by inconsistent particle to particle contact; however, both K migration and catalyst agglomeration were clearly demonstrated in the lab.

Example 2

High Steam-to-Ethylbenzene Molar Ratio Reactor Data

A typical shutdown procedure generally involves initially removing the flow of ethylbenzene, and subsequently replacing the flow of steam with nitrogen as the catalyst bed cools. In such a typical shutdown procedure, there is generally a significant period of time when the catalyst bed is at high temperature while in contact with only steam. For example, at the beginning of the shutdown procedure, steam and ethylbenzene flow across the catalyst bed as the reactor temperatures are lowered. At a temperature of about 538 to 580° C. (1000-1076° F.), the ethylbenzene flow is generally stopped. The temperature at which the flow of ethylbenzene is stopped may vary depending upon the catalyst used. The typical shutdown procedure will generally then include cooling under a steam-only flow until a temperature of about 425° C. (797° F.) is reached, and then the steam will be replaced by a circulating nitrogen purge. Without wishing to be bound by theory, the period of cooling under the steam-only flow may cause strengthening of the catalyst agglomeration as the melting point of KOH is 360° C. (680° F.).

Experiments to demonstrate the extent of dehydrogenation at lower temperatures and higher steam-to-ethylbenzene molar ratios were conducted in an isothermal reactor using a catalyst that includes potassium. The catalyst (57 mL) was ground and sieved to 8-14 mesh and loaded in a tubular metal reactor. The experiments were conducted at 0.4 LHSV and 765 mbar outlet pressure. The reaction conditions initially included a steam-to-ethylbenzene molar ratio of 7, before lowering the temperature and raising the steam-to-ethylbenzene molar ratio to 20 and 30. The temperature was lowered in stages down to 460° C. at a steam-to-ethylbenzene molar ratio of 20 then was raised in stages to a steam-to-ethylbenzene molar ratio of 30.

High steam-to-ethylbenzene molar ratio catalytic runs were conducted in the isothermal reactor to identify a range of temperatures where dehydrogenation of ethylbenzene to styrene occurs. Temperatures ranging from 460 to 560° C. (860 to 1040° F.) were evaluated at 20 and 30 steam-to-ethylbenzene molar ratios. The results are shown in FIG. 1. Conversion was observed down to 460° C. where there is still about 2% remaining. The steam-to-ethylbenzene molar ratio of 30 did not diverge much from the steam-to-ethylbenzene molar ratio of 20 at lower temperatures. The high steam-to-ethylbenzene molar ratio operating range extends down to about 450° C. (843° F.) based on extrapolation of the reactor data.

Example 3

A lab test was developed to study catalyst agglomeration using composite pellets prepared from used catalyst powders and potassium carbonate. The pellets were placed in a reactor and subjected to various conditions followed by crush strength testing of the experimental pellets. A high steam-to-ethylbenzene molar ratio sequence lessened catalyst agglomeration versus steam-only conditions at elevated temperatures.

Agglomeration Testing in the Isothermal Reactor

Test pellets were prepared from used catalyst powder and potassium carbonate. The powders were screened with a 14 mesh sieve and mixed in a 70:30 weight ratio of used catalysts to potassium carbonate. The mixture was pressed with a plunger die set at 2000 psi into a 13 mm diameter pellet using 1.5 g of powder mixture for each pellet. The pellet thickness was about 6.5 mm. The pellets (4 per experiment) were secured in a screen wire basket attached to the end of a supporting metal rod. A 1" reactor without an internal thermal well was used to test the 13 mm used catalyst/potassium carbonate pellets. This pellet preparation method was designed to simulate the state of catalyst in the reactors at the end of a run where there are external deposits of potassium mixed with used catalyst under the weight of a fully loaded reactor. Runs were also made with a 2" bed of used catalyst upstream from the test pellets in order to simulate a reaction stream with dehydrogenation products. Experiments 1-4, as detailed below, were conducted to simulate several different scenarios.

A catalyst crush test apparatus was used to gauge the strength of the pellets after removal from the reactor. The catalyst crush strength test apparatus included a metal plunger driven by high pressure nitrogen, and a pressure gauge on the nitrogen stream to record the pressure where the pellet is crushed. Due to the large cross section of the pellets, a 7 mm diameter metal rod was placed on the catalyst particle to lower the pressure needed to break apart the pellets. Stronger crush strength measurements indicate catalyst agglomeration, while reductions in crush strength indicate alleviation of catalyst agglomeration.

Experiment 1

Reference (Rapid Shutdown/$N_2$ Quench)

Four 13 mm pellets were put into a mesh basket and loaded into the reactor. The reactor was brought to reaction conditions and operated at reaction conditions for 2 days at 580° C., 750 mbar, and a steam-to-ethylbenzene molar ratio of 7. The temperature of the reactor was then lowered to 555° C., simulating a shutdown. The introduction of steam and ethylbenzene to the reactor was rapidly stopped, and the introduction of a nitrogen purge was begun. The temperature of the reactor was lowered to 360° C., and heated with nitrogen overnight. The pellets were cooled and unload for crush strength testing.

Experiment 2

Nitrogen Purge ($N_2$ Overnight Cooling)

Four 13 mm pellets were put into a mesh basket and loaded into the reactor. The reactor was brought to reaction conditions and operated under reaction conditions for 2 days at 580° C., 750 mbar, and a steam-to-ethylbenzene molar ratio of 7. The temperature of the reactor was lowered to 555° C., simulating a shutdown. The introduction of ethylbenzene and steam to the reactor was rapidly stopped, and the introduction of a nitrogen purge was begun. The temperature of the reactor was lowered to 500° C. and held at 500° C. for 18 hours with the nitrogen purge. Heating of the reactor was ceased, and the pellets were cooled and unloaded for crush strength testing.

Experiment 3

Steaming (Steam Cooling Overnight)

Four 13 mm pellets were put into a mesh basket and loaded into the reactor. The reactor was brought to reaction conditions and operated at reaction conditions for 2 days at 580° C., 750 mbar, and a steam-to-ethylbenzene molar ratio of 7. The temperature of the reactor was lowered to 555° C., and then the flow of ethylbenzene to the reactor was stopped. The temperature of the reactor was lowered to 500° C. while continuing the flow of steam to the reactor, and the reactor was maintained under these conditions for 18 hours. The introduction of the steam to the reactor was stopped. A nitrogen purge was introduced to the reactor, the temperature of the reactor was lowered 360° C., and the reactor was held at these conditions overnight. The pellets were cooled and then unloaded for crush strength testing.

Experiment 4

High Steam-to-Ethylbenzene Cooling

Four 13 mm pellets were put into a mesh basket and loaded into the reactor. About 2" of used catalyst were loaded upstream from the pellets. The reactor was brought to reaction conditions and operated at reaction conditions for 1 day at 580° C., 750 mbar, and a steam-to-ethylbenzene molar ratio of 7. The temperature of the reactor was lowered to 550° C., then the change the steam-to-ethylbenzene molar ratio was raised to 20:1, and cooling of the reactor was begun. The reactor was cooled to 450° C. through the day at the steam-to-ethylbenzene molar ratio of 20:1 and held overnight. In the morning, the flow of ethylbenzene was stopped, and the reactor was cooled to 360° C. The introduction of the steam to the reactor was stopped. A nitrogen purge was introduced to the reactor, and the reactor was held under nitrogen purge at 360° C. overnight. The pellets were cooled and then unloaded for crush strength testing. Table 1 depicts the crush strength test results for Experiments 1-4.

TABLE 1

Crush Strength Data from Shutdown Experiments

| Expt # | Experiment and Objective | Average Crush Strength |
|---|---|---|
| 1 | Nitrogen Quench/fast cooling for state of catalyst during the run | 20 |
| 2 | Nitrogen purge for inert gas effects | 31 |
| 3 | Steam purge for effects of standard shutdown procedure | 28 |
| 4 | High S/O purge for EB/$H_2$/$CO_2$ effects | 12 |

Increases in crush strength correlate with increasing catalyst agglomeration. Decreases in crush strength correlates with decreasing catalyst agglomeration. Experiment 1 was conducted to determine the status of the catalyst during the run by quenching the catalyst pellets with rapid cooling and a high flow of nitrogen. Experiment 1 serves as a reference point before initiating a shutdown procedure. In Experiment 2 the catalyst was subjected to a slow cool down with a nitrogen purge. A pellet strengthening was observed, that is the crush strength of the catalyst pellets was increased relative to Experiment 1. Experiment 3 most closely resembles a typical shutdown procedure under steam. Experiment 3 showed an increase in pellet crush strength. Experiment 4 evaluated a high steam-to-ethylbenzene molar ratio. The catalyst pellets in Experiment 4 exhibited a decrease in crush strength relative to Experiment 1. The catalyst pellets in Experiment 4 were noticeably weaker when handled.

The use of a high steam-to-ethylbenzene molar ratio, rather than steam-only, at temperatures ranging from 460 to 560° C. (860-1040° F.) brought about diminished catalyst agglomeration effects.

Example 4

Example 4 expanded upon the temperature range of the experiments in Example 3, and investigated the hydrogen effect with steam. The experiments of Example 4 used test pellets made from compressed used catalyst powder and potassium carbonate, as in Example 3. The pellets were loaded in the isothermal reactor downstream from a small catalyst bed and conditioned at typical run conditions.

Agglomeration Testing in the Isothermal Reactor

Test pellets were prepared from used catalyst powder of a promoted potassium and iron oxide industrial formulation and potassium carbonate. The powders were screened with a 14 mesh sieve and mixed in a 70:30 weight ratio of used catalysts to potassium carbonate. The mixture was pressed with a plunger die set at 2000 psi into a 13 mm diameter pellet using 1.5 g of powder mixture for each pellet. The pellet thickness was about 6.5 mm. The pellets were secured in a screen wire basket attached to the end of a supporting metal rod. A 1" reactor without an internal thermal well was used to test the 13 mm used catalyst/potassium carbonate pellets. Runs were also made with a 2" bed of used catalyst upstream from the test pellets in order to simulate a reaction stream with dehydrogenation products. The following experiments were conducted as described below to simulate several different scenarios. The catalyst crush test apparatus was used to gauge the strength of the pellets after removal from the reactor. Due to the large diameter of the test pellets, a 7 mm metal rod was placed on the pellet to lower the effective pressure that is required to break the pellets to a reasonable level.

Descriptions of Experiments 0 and 5-10 are provided below. The steam-only and the high steam-to-ethylbenzene molar ratio conditions were tested at 450° C., 500° C. and 550° C. (842° F., 932° F. and 1022° F.). Hydrogen was added with the steam in Experiment 6 to test the effects thereof. As a reference, catalyst pellets were heated overnight in an open air lab furnace, Experiment 0, to determine thermal effects.

Experiment 5

Steam Cooling with Catalyst Bed Upstream (500° C.)

Four 13 mm pellets were put into a mesh basket and loaded into the reactor. About 2" of used catalyst were loaded upstream from the pellets. The reactor was brought to reaction conditions and operated at reaction condition for 1 day at 580° C., 750 mbar, and a steam-to-ethylbenzene molar ratio of 7. A sample was taken to check conversion. The temperature of the reactor was lowered to 555° C., and then the flow of ethylbenzene was stopped. The temperature of the reactor was lowered to 500° C. while continuing the flow of steam, and these conditions were held for 18 hours. The flow of steam was stopped. A nitrogen purge was begun, the temperature was lowered to 360° C., and these conditions were held overnight. The pellets were cooled then unloaded for crush strength testing Experiment 6

Hydrogen/Steam Cooling

Four 13 mm pellets were put into a mesh basket and loaded into the reactor. About 2" of used catalyst were loaded upstream from the pellets. The reactor was brought to reaction conditions and operated at reaction conditions for 1 day at 580° C., 750 mbar, and a steam-to-ethylbenzene molar ratio of 7. The temperature of the reactor was lowered to 550° C., then a stream of hydrogen (550 sccm)/steam was introduced and cooling was begun. The reactor was cooled to 500° C. through the day under the hydrogen/steam flow and held overnight. In the morning, the flow of hydrogen was stopped, and the reactor was rapidly cooled to a temperature of 360° C. The flow of steam was stopped. A nitrogen purge was begun and held at 360° C. overnight. The pellets were cooled then unloaded for crush strength testing.

Experiment 7

Steam Cooling with Catalyst Bed Upstream (450° C.)

Four 13 mm pellets were put into a mesh basket and loaded into the reactor. About 2" of used catalyst were loaded upstream from the pellets. The reactor was brought to reaction conditions and operated under reaction conditions for 1 day at 580° C., 750 mbar, and a steam-to-ethylbenzene molar ratio of 7. A sample was taken to check the conversion. The reactor temperature was lowered to 555° C., and then the ethylbenzene flow was stopped. The reactor temperature was lowered to 450° C. while continuing the flow of steam, and these conditions were held for 18 hours. The flow of steam was stopped. A nitrogen purge was begun, the reactor temperature was lowered to 360° C., and these conditions were held overnight. The pellets were cooled then unloaded for crush strength testing.

Experiment 8

High Steam-to-Oil (S/O) Cooling (500° C.)

Four 13 mm pellets were put into a mesh basket and loaded into the reactor. About 2" of used catalyst were loaded upstream from the pellets. The reactor was brought to reaction conditions and operated at reaction conditions for 1 day at 580° C., 750 mbar, and a steam-to-ethylbenzene molar ratio of 7. The temperature of the reactor was lowered to 550° C., then the steam-to-ethylbenzene molar ratio was adjusted to 20:1, and cooling was begun. The reactor was cooled to 500° C. through the day at the steam-to-ethylbenzene molar ratio was adjusted to 20:1 and held overnight. In the morning, the flow of ethylbenzene was stopped and the reactor was cooled to 360° C. The flow of steam was stopped. A nitrogen purge was started and held at 360° C. overnight. The pellets were cooled and then unloaded for crush strength testing.

Experiment 9

Steam Cooling with Catalyst Bed Upstream (550° C.)

Four 13 mm pellets were put into a mesh basket and loaded into the reactor. About 2" of used catalyst were loaded upstream from the pellets. The reactor was brought to reaction conditions and operated at reaction conditions for 1 day at 580° C., 750 mbar, and a steam-to-ethylbenzene molar ratio of 7. A sample was taken to check the conversion. The reactor temperature was lowered to 550° C., and then the flow of ethylbenzene was stopped. The reactor temperature was maintained at 550° C. while continuing the flow of steam, and these conditions were held for 18 hours. The flow of steam was stopped. A nitrogen purge was begun, the reactor temperature was rapidly lowered to 360° C., and these conditions were held overnight. The pellets were cooled and then unloaded for crush strength testing.

Experiment 10

High Steam-to-Oil (S/O) Cooling (550° C.)

Four 13 mm pellets were put into a mesh basket and loaded into the reactor. About 2" of used catalyst were loaded upstream from the pellets. The reactor was brought to reaction conditions and operated at reaction conditions for 1 day at 580° C., 750 mbar, and a steam-to-ethylbenzene molar ratio of 7. The reactor temperature was lowered to 550° C., and then the steam-to-ethylbenzene molar ratio was adjusted to 20:1. The reactor was held at 550° C. with the flow having a steam-to-ethylbenzene molar ratio of 20:1 for 18 hours. In the morning, the flow of steam and ethybenzene was stopped, and the reactor was cooled rapidly to 360° C. The reactor was held at 360° C. overnight under a nitrogen purge. The pellets were cooled and then unloaded for crush strength testing.

Experiment 10

Thermal Treatment in Furnace with Air Atmosphere (470° C.)

Four 13 mm pellets were put into a ceramic dish. The ceramic dish with the pellets was put into an open air lab furnace heated at 475° F., and held under these conditions overnight. The pellets were cooled and then unloaded for crush strength testing.

The average crush strength for Experiments 0 and 5-10 are shown in Table 2 below. The standard deviation of the average crush strengths in Table 2 averaged 4 lb per data sheet.

TABLE 2

Summary of Experimental Results

| Expt # | Description | Average Crush Strength |
|---|---|---|
| 7 | Steam, 450° C. | 31 |
| 5 | Steam, 500° C. | 60 |
| 9 | Steam, 550° C. | 40 |
| 8 | High Steam-to-Ethylbenzene Molar Ratio, 500° C. | 23 |
| 10 | High Steam-to-Ethylbenzene Molar Ratio, 550° C. | 14 |

TABLE 2-continued

Summary of Experimental Results

| Expt # | Description | Average Crush Strength |
|---|---|---|
| 6 | Steam and $H_2$, 500° C. | 37 |
| 0 | Furnace, 475° C. | 39 |

Figure 2:
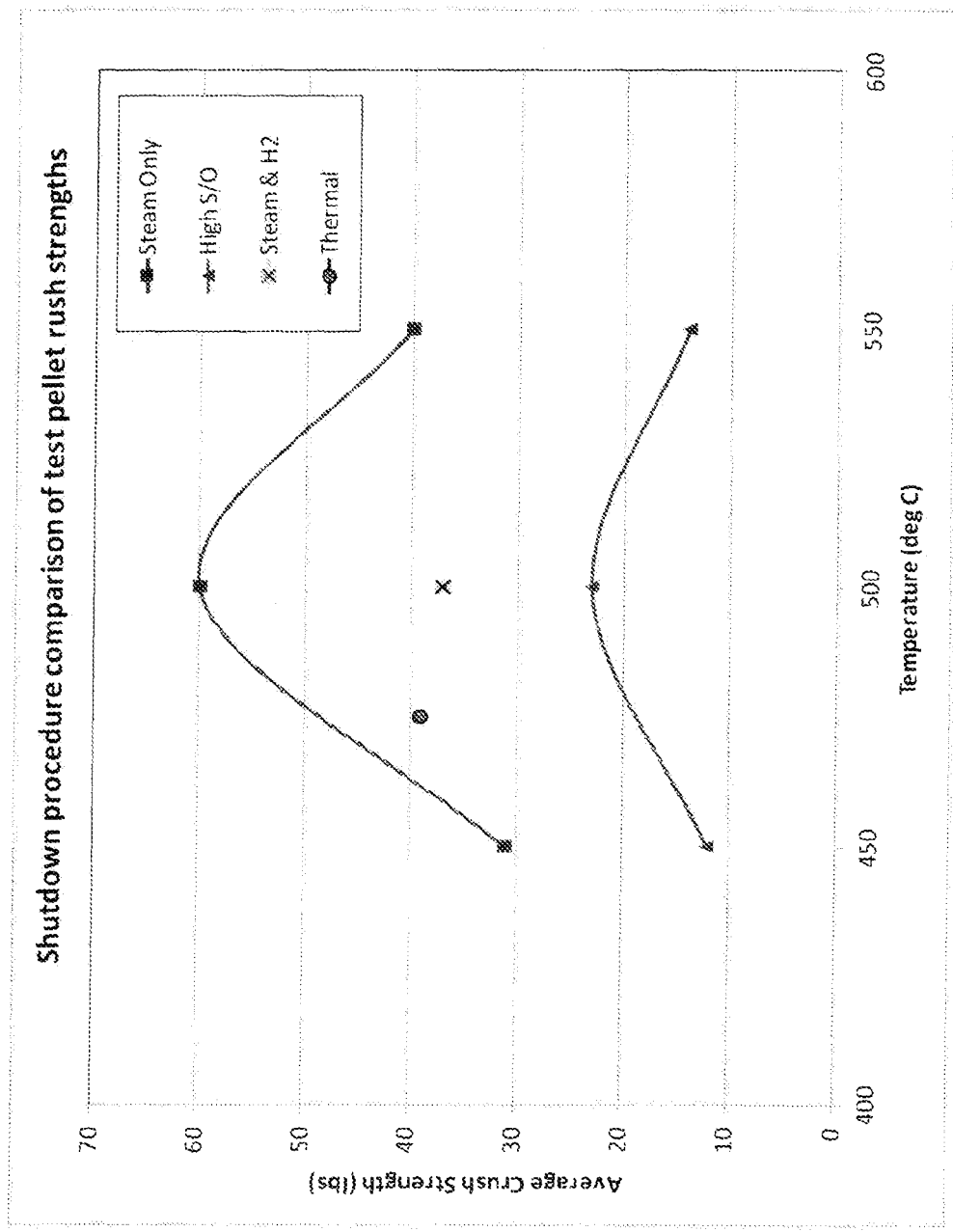
FIG. 2 depicts a plot of average crush strength versus temperature for different catalyst shutdown procedures.

The high steam-to-ethylbenzene molar ratio shutdown procedure is demonstrated to produce a lower pellet crush strength than the steam-only experiments at each temperature in the experimental range, as shown in FIG. 2. Both the high steam-to-ethylbenzene molar ratio shutdown procedure and the steam-only shutdown procedure showed maximum pellet strengths at 500° C. (932° F.), indicating that potassium migration and catalyst agglomeration is most severe at this temperature.

The results demonstrate that the traditional steam-only shutdown procedure may promote significant catalyst agglomeration, especially with the latest generation of catalysts and long run times of 30 to 42 months or longer. The high steam-to-ethylbenzene molar ratio shutdown procedure may cause the presence of aromatics, such as styrene, hydrogen and carbon dioxide in the dehydrogenation reactor system with the catalyst during the shutdown procedure. Carbon dioxide may convert KOH to potassium carbonate.

Experiment 0 demonstrates that the thermal effect provided lower average crush strength than the steam-only shutdown procedure, but higher average crush strength than that of the high steam-to-ethylbenzene molar ratio shutdown procedure. This is consistent with a steam promotion effect for catalyst agglomeration.

Diminished catalyst agglomeration was observed when hydrogen ($H_2$) was added to the steam. Without wishing to be bound by theory, the presence of hydrogen may cause coke removal, iron oxide reduction, KOH inhibition, or combinations thereof, which may reduce catalyst agglomeration.

Depending on the context, all references herein to the "disclosure" may in some cases refer to certain specific embodiments only. In other cases it may refer to subject matter recited in one or more, but not necessarily all, of the claims. While the foregoing is directed to embodiments, versions and examples of the present disclosure, which are included to enable a person of ordinary skill in the art to make and use the disclosures when the information in this patent is combined with available information and technology, the disclosures are not limited to only these particular embodiments, versions and examples. Other and further embodiments, versions and examples of the disclosure may be devised without departing from the basic scope thereof and the scope thereof is determined by the claims that follow.

What is claimed is:

1. A process comprising:
   shutting down a reactor wherein ethylbenzene is undergoing dehydrogenation to styrene in the presence of steam and a catalyst adapted to catalyze dehydrogenation of ethylbenzene to styrene, wherein shutting down the reactor comprises:
   reducing a temperature of the reactor;
   increasing a steam-to-ethylbenzene molar ratio of an input stream to the reactor to form a purge stream; and
   supplying the purge stream to the reactor.

2. The process of claim 1, wherein shutting down the reactor is performed without use of a steam-only purge stream.

3. The process of claim 1, further comprising, after supplying the purge stream to the reactor, further reducing the temperature of the reactor.

4. The process of claim 3, further comprising continuing to supply the purge stream to the reactor while further reducing the temperature of the reactor.

5. The process of claim 3, further comprising stopping supply of the purge stream to the reactor before further reducing the temperature of the reactor.

6. The process of claim 3, further comprising stopping supply of the purge stream to the reactor and supplying an inert gas purge stream to the reactor.

7. The process of claim 6, further comprising, after supplying the inert gas purge stream to the reactor, further reducing the temperature of the reactor.

8. The process of claim 1, further comprising stopping introduction of ethylbenzene to the reactor to form a steam-only purge stream, and supplying the steam-only purge stream to the reactor.

9. The process of claim 8, wherein the temperature of the reactor is further reduced after supplying the steam-only purge stream to the reactor.

10. The process of claim 1, wherein the purge stream has a steam-to-ethylbenzene molar ratio of from 12:1 to 50:1.

11. The process of claim 1, wherein the temperature of the reactor is reduced to range from less than 650° C. to 360° C.

12. The process of claim 1, wherein the steam-to-ethylbenzene molar ratio of the purge stream is continuously maintained at from 12:1 to 50:1 while the temperature of the reactor is within the range of 550° C. to 450° C. during the shutting down of the reactor.

13. The process of claim 1, wherein the catalyst comprises potassium promoted iron oxide.

14. The process of claim 1, wherein, after shutting down the reactor, the catalyst or agglomerated catalyst particles thereof exhibits an average crush strength that is lower than an average crush strength exhibited by the catalyst prior to shutting down the reactor.

15. The process of claim 1, wherein the steam-to-ethylbenzene molar ratio of the purge stream is continuously maintained at from 12:1 to 50:1 from the time at which the purge stream is introduced into the reactor until the purge stream is replaced with an inert gas purge stream.

16. A process comprising:
shutting down a reactor wherein ethylbenzene is undergoing dehydrogenation to styrene in the presence of a catalyst adapted to catalyze dehydrogenation of ethylbenzene to styrene, wherein the catalyst comprises potassium, wherein shutting down the reactor comprises:
reducing a temperature of the reactor;
increasing a steam-to-ethylbenzene molar ratio of an input stream to the reactor to form a purge stream;
supplying the purge stream to the reactor; and
stopping supply of the purge stream to the reactor and supplying an inert gas purge stream to the reactor, wherein shutting down the reactor is performed without use of a steam-only purge stream.

17. A process comprising:
shutting down a reactor wherein ethylbenzene is undergoing dehydrogenation to styrene in the presence of a catalyst adapted to catalyze dehydrogenation of ethylbenzene to styrene, wherein shutting down the reactor comprises:
reducing a temperature of the reactor; and
supplying a purge stream to the reactor comprising steam, wherein the purge stream further comprises $H_2$, $CO_2$, styrene, or combinations thereof.

18. The process of claim 17, wherein the purge stream further comprises $H_2$.

19. The process of claim 17, wherein the purge stream further comprises $CO_2$.

20. The process of claim 17, wherein the purge stream further comprises styrene.

* * * * *